United States Patent [19]

Franckowiak et al.

[11] Patent Number: 4,710,501

[45] Date of Patent: Dec. 1, 1987

[54] CIRCULATION ACTIVE PYRIMIDINYL-DIHYDROPYRIDINES

[75] Inventors: Gerhard Franckowiak; Martin Bechem; Rainer Gross, all of Wuppertal; Michael Kayser, Hagen; Matthias Schramm, Cologne, all of Fed. Rep. of Germany; Günter Thomas, Milan, Italy

[73] Assignee: Bayer Aktiengesellschaft, Leverkusen, Fed. Rep. of Germany

[21] Appl. No.: 862,869

[22] Filed: May 13, 1986

[30] Foreign Application Priority Data

May 15, 1985 [DE] Fed. Rep. of Germany ....... 3517473

[51] Int. Cl.⁴ .................... A61K 31/44; C07D 401/04; C07D 239/24
[52] U.S. Cl. .................................. 514/256; 514/274; 514/275; 544/316; 544/331; 544/333
[58] Field of Search ...................... 544/316, 331, 333; 514/256, 274, 275

[56] References Cited

U.S. PATENT DOCUMENTS 4,248,873  2/1981  Bossert et al. ...................... 544/333

OTHER PUBLICATIONS

Goodman et al., The Pharmacological Basis of Therapeutics, 6th ed., p. 28.

Primary Examiner—Henry R. Jiles
Assistant Examiner—J. Richter
Attorney, Agent, or Firm—Sprung Horn Kramer & Woods

[57] ABSTRACT

Novel compounds of the formula

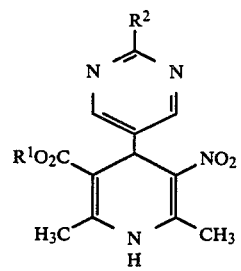

in which
  $R^2$ is hydrogen or a substituent, and
  $R^1$ is optionally substituted alkyl or alkenyl,
exhibit positive inotropic activity on the cardiac muscle, intensifying the contraction power.

7 Claims, No Drawings

CIRCULATION ACTIVE PYRIMIDINYL-DIHYDROPYRIDINES

The invention relates to 4-pyrimidinyl-1,4-dihydropyridines, processes for their preparation and their use in medicaments, in particular in medicaments which influence the circulation.

It is known that 1,4-dihydropyridines, as calcium antagonists, effect inhibition of the contraction power of smooth and cardiac muscles and can be used for the treatment of coronary and vascular diseases [compare A. Fleckenstein, Am. Rec. Pharmacol. Toxicol. 17, 149–166 (1977)].

Knowing these properties of dihydropyridines, it was not to be expected that the compounds according to the invention from this class of substance have no contraction-inhibiting action but have the effect of intensifying the contraction power and a positively inotropic action on the cardiac muscle.

The present invention relates to 4-pyrimidinyl-1,4-dihydropyridines of the general formula I

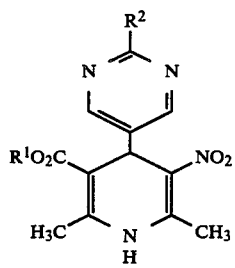

in which
  $R^1$ represents straight-chain, branched or cyclic alkyl or alkenyl with up to 10 C atoms which is optionally substituted by $C_6$–$C_{10}$-aryl, $C_6$–$C_{10}$-aryloxy, $C_6$–$C_{10}$-arylthio, cyano, nitro, hydroxyl, halogen, $C_1$–$C_8$-alkoxy, $C_1$–$C_8$-alkylthio, $C_1$–$C_8$-alkylsulphonyl, trifluoromethoxy, trifluoromethylthio, carboxyl, $C_1$–$C_6$-alkoxycarbonyl, saturated or unsaturated 5 to 7-membered heterocyclyl which is optionally substituted by halogen, $C_1$–$C_4$-alkyl or $CF_3$ and has one or more hetero-atoms, such as O, S or N, a group of the formulae

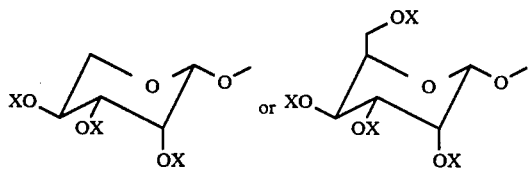

in which
  X represents hydrogen or acetyl,
  or is substituted by an amino group of the formula

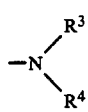

wherein
  $R^3$ and $R^4$ are identical or different and represent hydrogen, or represent $C_6$–$C_{10}$-aryl, or represent $C_7$–$C_{14}$-aralkyl, or represent $C_1$–$C_6$-alkyl, or represent $C_2$–$C_7$-acyl, and
  $R^2$ represents hydrogen, or represents straight-chain, branched or cyclic alkyl or alkenyl which has up to 8 C atoms and is optionally substituted by halogen or cyano, or represents halogen, or represents $C_6$–$C_{10}$-aryl, or represents $C_1$–$C_6$-alkoxy, or represents an amino group of the formula

wherein
  $R^5$ and $R^6$ are identical or different and represent hydrogen, $C_1$–$C_8$-alkyl, $C_2$–$C_8$-alkenyl, $C_5$–$C_8$-cycloalkyl, $C_6$–$C_{10}$-aryl, $C_7$–$C_{14}$-aralkyl, $C_2$–$C_7$-acyl, $C_1$–$C_3$-$SO_2$-alkyl or -$SO_2$-phenyl,
or wherein
  these substituents optionally form a 5–7-membered ring, which can contain oxygen, sulphur and/or nitrogen as further hetero-atoms, with the nitrogen atom,
and physiologically acceptable salts thereof.

Preferred compounds of the general formula I are those in which
  $R^1$ represents straight-chain, branched or cyclic alkyl or alkenyl with up to 8 C atoms, which is optionally substituted by phenyl, phenoxy, phenylthio, cyano, hydroxyl, one or more fluorine, chlorine or bromine, $C_1$–$C_6$-alkoxy, $C_1$–$C_6$-alkylthio, trifluoromethoxy, carboxyl, $C_1$–$C_4$-alkoxycarbonyl, pyridyl, thienyl, furyl, piperidinyl, piperazinyl, morpholinyl, tetrazolyl, thiadiazolyl, pyrimidinyl, pyrrolidinyl or triazolyl, it being possible for the heterocyclic radicals optionally to be substituted by fluorine, chlorine, methyl or trifluoromethyl, or by a group of the formulae

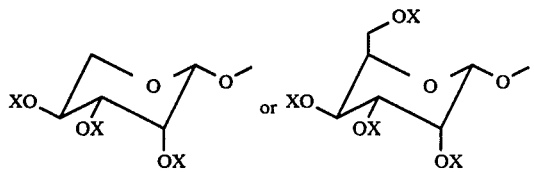

in which
  X represents hydrogen or acetyl,
  or is substituted by an amino group of the formula

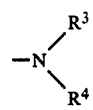

wherein
  $R^3$ and $R^4$ are identical or different and represent hydrogen, or represent phenyl, or represent benzyl, or represent $C_1$–$C_4$-alkyl, or represent benzoyl or acetyl, and
  $R^2$ represents hydrogen, or represents straight-chain, branched or cyclic alkyl or alkenyl which has up to 6 C atoms and is optionally substituted by one or more fluorine, chlorine, bromine or cyano, or represents fluorine, chlorine or bromine, or represents phenyl, or represents $C_1-C_4$-alkoxy, or represents an amino group of the formula

wherein $R^5$ and $R^6$ are identical or different and (optionally) represent hydrogen, $C_1-C_6$-alkyl, $C_2-C_6$-alkenyl, $C_5-C_7$-cycloalkyl, phenyl, benzyl, benzoyl or acetyl, or wherein these substituents form a 5 to 6-membered ring, which can contain oxygen, sulphur or nitrogen as a further hetero-atom, and physiologically acceptable salts thereof.

Particularly preferred compounds of the general formula I are those in which $R^1$ represents straight-chain, branched or cyclic alkyl or alkenyl with up to 6 C atoms, which is optionally substituted by phenyl, cyano, hydroxyl or one or more fluorine atoms, by $C_1-C_4$-alkoxy, pyridyl, thienyl, furyl, pyrimidinyl, piperidinyl, piperazinyl or morpholinyl, by a group of the formula

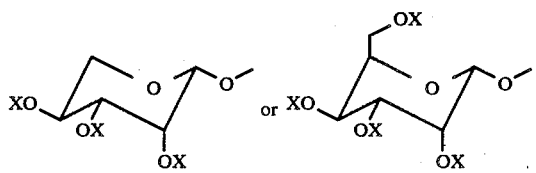

in which

X represents hydrogen or acetyl, or is substituted by an amino group of the formula

wherein $R^3$ and $R^4$ are identical or different and represent hydrogen, or represent phenyl, or represent benzyl, or represent $C_1-C_3$-alkyl, and $R^2$ represents hydrogen, or represents straight-chain or branched alkyl or alkenyl which has up to 4 C atoms and is optionally substituted by one or more fluorine atoms, or represents fluorine or chlorine, or represents methoxy, or represents an amino group of the formula

wherein $R^5$ and $R^6$ are identical or different and represent $C_1-C_4$-alkyl, $C_2-C_4$-alkenyl, cyclohexyl, cyclopentyl, phenyl, benzyl or acetyl, or wherein the substituents form a piperazine, piperidine, morpholine, thiomorpholine or pyrrolidine ring, and physiologically acceptable salts thereof.

The compounds according to the invention have useful pharmacological properties. They are vasodilating and positively inotropic and thus represent an enrichment of pharmacy.

Physiologically acceptable salts can be salts of the compounds according to the invention with inorganic or organic acids. An example which may be mentioned are: salts with mineral acids, such as hydrogen halide acids, sulphuric acid or phosphoric acid, or with organic acids, such as, for example, formic acid, acetic acid, maleic acid, fumaric acid, tartaric acid, malic acid, citric acid, lactic acid or benzoic acid.

The compounds according to the invention exist in stereoisomeric forms which either behave as mirror images (enantiomers) or do not behave as mirror images (diastereomers). The invention relates both to the antipodes and to the racemic forms as well as to diastereomer mixtures. The racemic forms, like the diastereomers, can be resolved in a known manner into the stereoisomerically uniform constituents (compare E. L. Eliel, Stereochemisty of Carbon Compounds, McGraw Hill, 1962).

The compounds of the general formula I according to the invention in which $R^1$ and $R^2$ have the abovementioned meaning are obtained by a process in which

[A] aldehydes of the general formula II

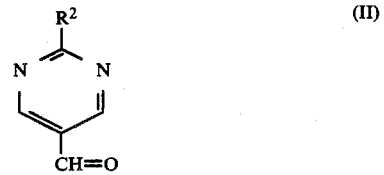

in which $R^2$ has the abovementioned meaning, and keto compounds of the general formula III

in which $R^1$ has the abovementioned meaning, are reacted with the compound of the formula IV

and ammonia, if appropriate in the presence of water or inert organic solvents, or in which

[B] aldehydes of the general formula (II) are reacted with keto compounds of the general formula (III) and the enamine of the formula (V)

if appropriate in the presence of water or inert organic solvents, or in which

[C] aldehydes of the general formula (II) are reacted with the keto compound of the formula (IV) and enamines of the general formula (VI)

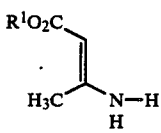

in which

R¹ has the abovementioned meaning,
if appropriate in the presence of water or inert organic solvents, or in which

[D] keto compounds of the general formula (III) are reacted with ammonia and ylidene compounds of the general formula (VII)

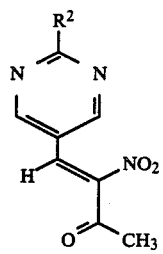

in which

R² has the abovementioned meaning,
if appropriate in the presence of water or inert organic solvents, or in which

[E] the keto compound of the formula (IV) is reacted with ammonia and ylidene compounds of the general formula (VIII)

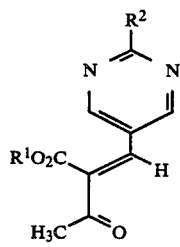

in which

R¹ and R² have the abovementioned meaning,
if appropriate in the presence of water or inert organic solvents, or in which

[F] ylidene compounds of the general formula (VII) are reacted with enamines of the general formula (VI), if appropriate in the presence of water or inert organic solvents, or in which

[G] ylidene compounds of the general formula (VIII) are reacted with the enamine of the formula (V), if appropriate in the presence of water or inert organic solvents.

Depending on the nature of the starting substances used, the syntheses can be represented by the following equations:

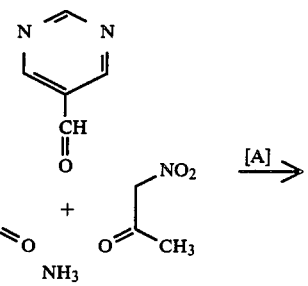

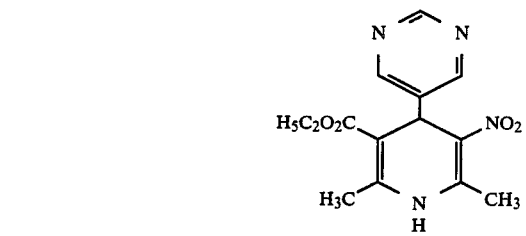

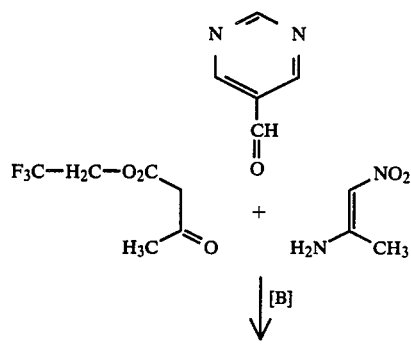

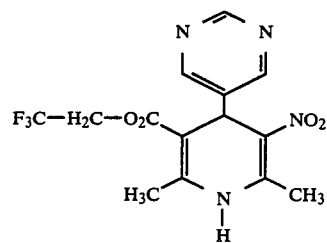

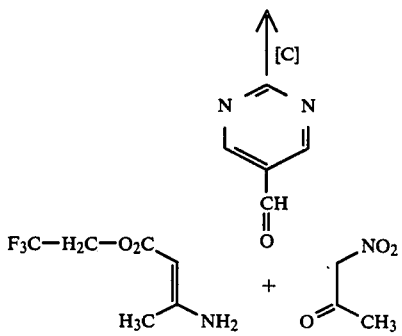

-continued

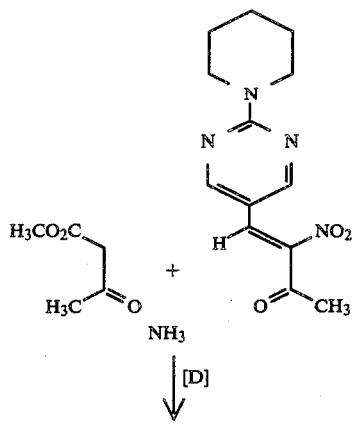

[D]

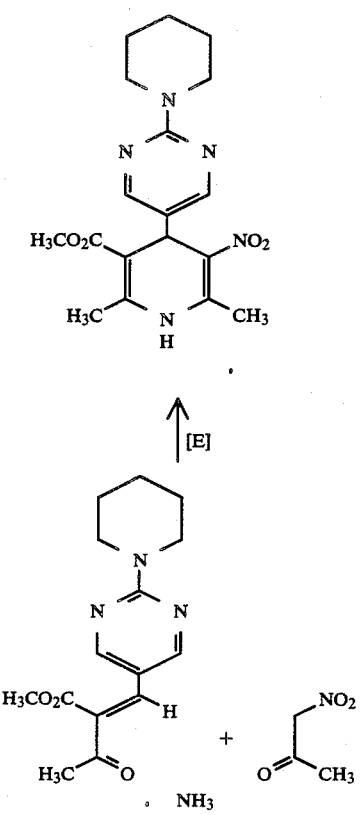

[F]

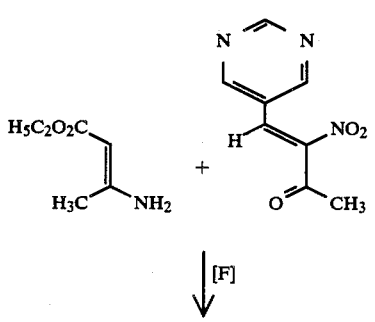

-continued

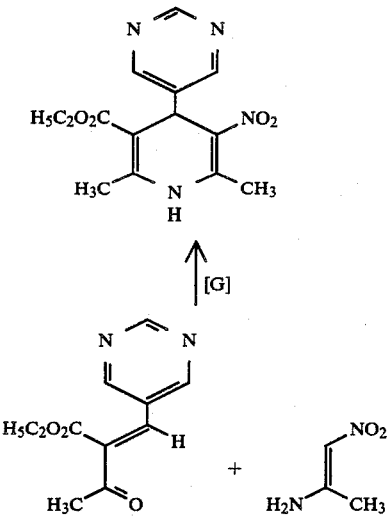

The compounds of the formulae II–VIII are known or can be prepared by methods which are known from the literature. In this context, compare: Aldehyde II: D. J. Brown, The Chemistry of Heterocyclic Compounds, Volume "Pyrimidine, Suppl. I", Wiley Interscience, 1970; Keto Compounds III: D. Borrmann, Houben-Weyl "Methoden der organischen Chemie" ("Methods of Organic Chemistry") Volume VII/4, 230 et seq., (1968); Keto Compounds IV: N. Levy, C. W. Scaife, J. Chem. Soc. (London) 1946, 1100; and C. D. Hurd, M. E. Nilson, J. Org. Chem. 20, 927 (1955); Enamines V: H. Böhme, K. H. Weisel, Arch. Pharm. 310, 30 (1977); Enamines VI: S. A. Glickman, A. C. Cope, J. Am. Chem. Soc. 67, 1017 (1945); Ylidene Compounds VII: A. Dornow, W. Sassenberg, Liebigs Ann. Chem. 602, 14 (1957); and Ylidene Compounds VIII: Organic Reactions XV, 204 (1967).

Possible diluents for all the processes are water or all inert organic solvents. These include, preferable, alcohols, such as methanol, ethanol, propanol, or isopropanol, ethers, such as diethyl ether, dioxane, tetrahydrofuran or glycol monomethyl ether, glacial acetic acid, pyridine, dimethylformamide, acetonitrile, dimethylsulphoxide or hexamethylphosphoric acid triamide.

The reaction temperatures can be varied within a substantial range for all the processes. The reactions are in general carried out in a range from 10° C. to 200° C., preferably from 20° C. to 150° C.

The reaction can be carried out under normal pressure, but also under increased pressure. It is in general carried out under normal pressure.

In carrying out the processes according to the invention, any desired ratio of the substances participating in the reaction may be used. In general, however, the processes are carried out with molar amounts of the reactants.

The above preparation processes are given merely for illustration. The preparation of the compounds of the formula I is not limited to these processes, but any modification of these processes can be applied in the same manner to the preparation of the compounds according to the invention.

The compounds according to the invention have a positive inotropic action and thus exhibit a useful pharmacological action spectrum which cannot be predicted. They can be used as agents which influence the circulation, as coronary therapeutics, antiarrhythmics and antihypotonics, and for the treatment of cardiac insufficiency.

The cardiac and vascular actions have been found on the isolated perfused heart of the guineapig.

The hearts of albino guineapigs weighing 250 to 350 g are used for this. The animals are sacrificed with a blow on the head, the thorax is opened, a metal cannula is inserted into the exposed aorta and the left auricle is opened. The heart is removed from the thorax with the lungs and connected via the aorta cannula to the perfusion apparatus with continuous perfusion. The lungs are removed at the lung roots. Krebs-Henseleit solution (1) (118.5 mmol/l of NaCl, 4.75 mmol/l of KCl, 1.19 mmol/l of KH$_2$PO$_4$, 119 mmol/l of MgSO$_4$, 25 mmol/l of NaHCO$_3$ and 0.013 mmol/l of NaEDTA), in which the CaCl$_2$ is varied as required but is as a rule 1.2 mmol/l, is used as the perfusion medium. 10 mmol/l of glucose are added as a substrate which supplies energy. Before perfusion, the solution is filtered free from particles. The solution is gassed with carbogen (95% O$_2$, 5% CO$_2$ to maintain the pH value of 7.4). The hearts are perfused at a constant flow (10 ml/minute) at 32° C. by means of a roller squeezing pump.

To measure the cardiac function, a latex bulb which is filled with liquid and is connected to a pressure transducer via a column of liquid is inserted into the left ventricle through the left auricle and the isovolumetric contractions are recorded on a high-speed recorder. (Opie, L., J. Physiol. 180 (1965) 529–541). The perfusion pressure is recorded by means of a pressure transducer connected to the perfusion system before the heart. Under these conditions, a reduction in perfusion pressure indicates coronary dilation and an increase in the left ventricular pressure amplitude indicates an increase in heart contractility. The compounds according to the invention are infused in suitable dilution into the perfusion system just before the isolated heart.

The following values show, by way of example, the contractility-increasing effect of the compounds according to the invention on the isolated perfused guineapig heart:

| Example No. | Concentration [g/ml] | Percentage change in contraction amplitude |
|---|---|---|
| 1 | 10$^{-7}$ | +5 |
| 1 | 10$^{-6}$ | +22 |
| 1 | 10$^{-5}$ | +89 |

The new active compounds can be converted in a known manner into the customary formulations, such as tablets, capsules, dragees, pills, granules, aerosols, syrups, emulsions, suspensions and solutions, using inert, non-toxic, pharmaceutically suitable excipients or solvents. The therapeutically active compound should in each case be present here in a concentration of about 0.5 to 90% by weight of the total mixture, that is to say in amounts which are sufficient to achieve the stated dosage range.

The formulations are prepared, for example, by extending the active compounds with solvents and/or excipients, if appropriate using emulsifying agents and-/or dispersing agents, and, for example, in the case of the use of water as the diluent, organic solvents can be used, if appropriate, as auxiliary solvents.

Examples of auxiliary substances which may be mentioned are: water, non-toxic organic solvents, such as paraffins (for example petroleum fractions), vegetable oils (for example groundnut/sesame oil), alcohols (for example ethyl alcohol and glycerol) and glycols (for example propylene glycol and polyethylene glycol), solid excipients, such as, for example, natural rock powders (for example kaolins, aluminas, talc and chalk), synthetic rock powders (for example highly disperse silicic acid and silicates) and sugars (for example sucrose, lactose and glucose), emulsifying agents (for example polyoxyethylene fatty acid esters), polyoxyethylene fatty alcohol ethers (for example lignin, sulphite waste liquors, methylcellulose, starch and polyvinylpyrrolidone) and lubricants (for example magnesium stearate, talc, stearic acid and sodium sulphate).

Administration is effected in the customary manner, preferably orally or parenterally, in particular perlingually or intravenously. In the case of oral use, tablets can of course also contain, in addition to the excipients mentioned, additives such as sodium citrate, calcium carbonate and dicalcium phosphate, together with various adjuvants, such as starch, preferably potato starch, gelatine and the like. Lubricants, such as magnesium stearate, sodium laurylsulphate and talc, can furthermore be co-used for tablet-making. In the case of aqueous suspension and/or elixirs intended for oral use, various flavor-improving agents or colorants can be added to the active compounds, in addition to the abovementioned auxiliary substances.

In the case of parenteral use, solutions of the active compounds can be employed, using suitable liquid excipients.

In general, it has proved advantageous, in the case of intravenous administration, to administer amounts of about 0.001 to 1 mg/kg, preferably about 0.01 to 0.5 ml/kg of body weight to achieve effective results. In the case of oral administration, the dosage is about 0.01 to 20 mg/kg, preferably 0.1 to 10 mg/kg of body weight.

Nevertheless, it may at times be necessary to deviate from the amounts mentioned, and in particular to do so as a function of the body weight of the experimental animal or of the nature of administration, but also because of the species of animal and its individual behavior towards the medicament or the nature of its formulation and the time or interval at which administration takes place. Thus, in some cases it can suffice to manage with less than the abovementioned minimum amount, whilst in other cases the upper limit mentioned must be exceeded. Where relatively large amounts are administered, it may be advisable to divide these into several individual doses over the day. The same dosage range is envisaged for administration in human medicine. The above statements also apply here in the general sense.

PREPARATION EXAMPLES

General working instructions A 10 mmol of pyrimidine-5-carbaldehyde, 10 mmol of β-aminocrotonic acid ester and 20 mmol of nitroacetone are heated to 60° C. in 20 mol of i-propanol for 4 hours. After the solvent has been evaporated off, the residue is chromatographed on silica gel with CHCl$_3$ containing 5% of methanol. The evaporated product fractions are crystallized from i-propanol/petroleum ether.

General working instructions B 10 mmol of 2-nitro-1-(pyrimidin-5-yl)but-1-en-3-one and 10 mmol of β-aminocrotonic acid ester are heated to 60° C. in 15 ml of i-propanol for 3 hours. The end products in some cases crystallize out directly. Otherwise, chromatographic working up is carried out as in working instructions A.

General working instructions C 10 mmol of α-acetyl-β-(pyrimidin-5-yl)acrylic acid ester and 15 mmol of NH$_3$-nitroacetone complex (corresponds to 2-amino-1-nitroprop-1-ene) are heated at 60° C. in 15 ml of i-propanol for 3 hours. The end products in some cases crystallize out directly. Otherwise, chromatographic working up is carried out as in working instructions A.

2-Nitro-1-(pyrimidin-5-yl)but-1-en-3-one derivatives (instructions B) and α-acetyl-β-(pyrimidin-5-yl)acrylic acid esters (instructions C) are prepared by customary methods by direct condensation of acetoacetates with pyrimidine-5-carbaldehydes under acid catalysis.

The compounds listed in the following table were prepared by all the processes described above.

(I)

[Structure: 4-pyrimidinyl-1,4-dihydropyridine core with R$^1$O$_2$C and NO$_2$ substituents, H$_3$C and CH$_3$ groups, NH in dihydropyridine ring, and R$^2$ on pyrimidine]

| Example No. | R$^1$ | R$^2$ | Melting point [°C.] |
|---|---|---|---|
| 1 | —CH$_2$—CH$_2$—(pyridin-2-yl) | H | 190 |
| 2 | —CH(CH$_3$)$_2$ | H | 240 |
| 3 | —(CH$_2$)$_3$—CH$_3$ | H | 210 |
| 4 | —CH$_2$—CH$_3$ | H | 250 |
| 5 | —CH$_2$—CH$_2$—CN | H | 222 |
| 6 | —CH$_2$—CF$_3$ | H | 227 |
| 7 | —(CH$_2$)$_2$—N(CH$_3$)CH$_2$—(phenyl) | H | 222 |
| 8 | —CH$_3$ | —NH—CH$_2$—CH=CH$_2$ | 226 |
| 9 | —CH$_3$ | —N(piperidinyl) | 244 |
| 10 | (triacetyl sugar)—O—(CH$_2$)$_3$— | H | resin |
| 11 | (triacetyl sugar)—O—(CH$_2$)$_2$— | H | resin |

It will be understood that the specification and examples are illustrative but not limitative of the present invention and that other embodiments within the spirit and scope of the invention will suggest themselves to those skilled in the art.

We claim:

1. A 4-pyrimidinyl-1,4-dihydropyridine of the formula

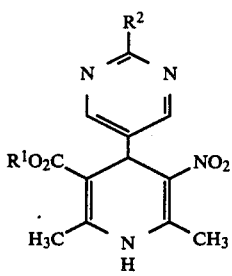

in which
R[1] represents straight-chain, branched or cyclic alkyl or alkenyl with up to 8 C atoms, which is optionally substituted by phenyl, phenoxy, phenylthio, cyano, hydroxyl, one or more fluorine, chlorine or bromine, by $C_1$-$C_6$-alkoxy, $C_1$-$C_6$-alkylthio, trifluoromethoxy, carboxyl, $C_1$-$C_4$-alkoxycarbonyl, or pyridyl, optionally substituted by fluorine, chlorine, methyl or trifluoromethyl, or by a group of the formulae

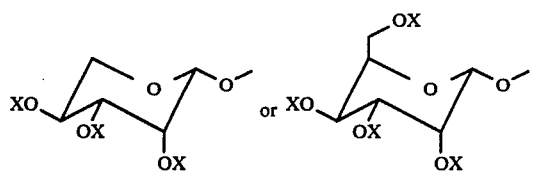

in which
X represents hydrogen or acetyl,
or is substituted by an amino group of the formula

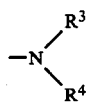

wherein
R[3] and R[4] are identical or different and represent hydrogen, or represent phenyl, or represent benzyl, or represent $C_1$-$C_4$-alkyl, or represent benzoyl or acetyl, and
R[2] represents hydrogen, or represents straight-chain, branched or cyclic alkyl or alkenyl which has up to 6 C atoms and is optionally substituted by one or more fluorine, chlorine, bromine or cyano, or represents fluorine, chlorine or bromine, or represents phenyl, or represents $C_1$-$C_4$-alkoxy, or represents an amino group of the formula

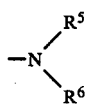

wherein
R[5] R[6] are identical or different and (optionally) represent hydrogen, $C_1$-$C_6$-alkyl, $C_2$-$C_6$-alkenyl, $C_5$-$C_7$-cycloalkyl, phenyl, benzyl, benzoyl or acetyl.

2. A compound or salt according to claim 1, in which R[1] represents straight-chain, branched or cyclic alkyl or alkenyl with up to 6 C atoms, which is optionally substituted by phenyl, cyano, hydroxyl or one or more fluorine atoms, by $C_1$-$C_4$-alkoxy, pyridyl, by a group of the formulae

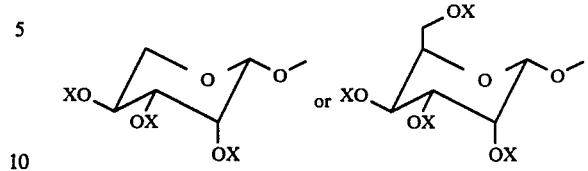

in which
X represents hydrogen or acetyl,
or is substituted by an amino group of the formula

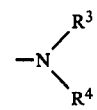

wherein
R[3] and R[4] are identical or different and represent hydrogen, or represent phenyl, or represent benzyl, or represent $C_1$-$C_3$-alkyl, and
R[2] represents hydrogen, or represents straight-chain or branched alkyl or alkenyl which has up to 4 C atoms and is optionally substituted by one or more fluorine atoms, or represents fluorine or chlorine, or represents methoxy, or represents an amino group of the formula

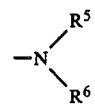

wherein
R[5] and R[6] are identical or different and represent hydrogen $C_1$-$C_4$-alkyl, $C_2$-$C_4$-alkenyl, cyclohexyl, cyclopentyl, phenyl, benzyl or acetyl.

3. A compound according to claim 1, wherein such compound is 2,6-dimethyl-5-nitro-3-[2(pyrid-2-yl)ethoxy]-carbonyl-4-(pyrimidin-5-yl)-1,4-dihydropyridine of the formula

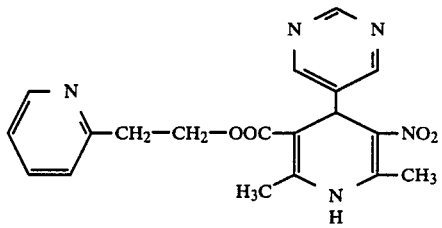

or a physiologically acceptable salt thereof.

4. A positively inotropic composition comprising an amount effective therefor of a compound or salt according to claim 1 in admixture with a diluent.

5. A unit dose of a composition according to claim 4 in the form of a tablet, capsule or ampule.

6. A method of evoking a positive inotropic effect in a patient which comprises administering to such patient an amount effective therefor of a compound or salt according to claim 1.

7. The method according to claim 6, wherein such compound is 2,6-dimethyl-5-nitro-3-[2(pyrid-2-yl)e- thoxy]-carbonyl-4-(pyrimidin-5-yl)-1,4-dihydropyridine
of the formula
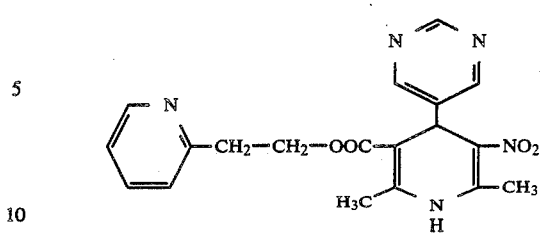
or a physiologically acceptable salt thereof.